US008652096B2

(12) United States Patent
Alvey et al.

(10) Patent No.: US 8,652,096 B2
(45) Date of Patent: Feb. 18, 2014

(54) COMPRESSIBLE MULTI-CHAMBER FEEDING TUBE DELIVERY DEVICE AND METHODS

(75) Inventors: John D. Alvey, Evansville, IN (US); Marc S. Velmer, Evansville, IN (US)

(73) Assignee: Mead Johnson Nutrition Company, Glenview, IL (US)

( * ) Notice: Subject to any disclaimer, the term of this patent is extended or adjusted under 35 U.S.C. 154(b) by 319 days.

(21) Appl. No.: 13/031,297

(22) Filed: Feb. 21, 2011

(65) Prior Publication Data

US 2012/0215203 A1 Aug. 23, 2012

(51) Int. Cl.
*A61M 5/14* (2006.01)

(52) U.S. Cl.
USPC ............. 604/81; 604/516; 604/518; 604/520; 604/257; 604/262; 604/410; 604/411; 604/414; 604/415

(58) Field of Classification Search
USPC ........... 604/514, 516, 518, 80, 81, 87, 88, 91, 604/191, 257, 262, 408, 410, 411, 414, 415, 604/520
See application file for complete search history.

(56) References Cited

U.S. PATENT DOCUMENTS

| | | | | | |
|---|---|---|---|---|---|
| 4,863,454 | A * | 9/1989 | LaBove | ........................ | 604/416 |
| 5,637,087 | A * | 6/1997 | O'Neil et al. | ................... | 604/82 |
| 6,039,720 | A * | 3/2000 | Wieslander | .................. | 604/410 |
| 7,488,307 | B2 * | 2/2009 | Rimlinger et al. | ............ | 604/197 |
| 2009/0326475 | A1 * | 12/2009 | Carlyon | ........................ | 604/191 |

* cited by examiner

*Primary Examiner* — Bhisma Mehta
(74) *Attorney, Agent, or Firm* — Waddey & Patterson, P.C.; James R. Cartiglia; Matthew C. Cox

(57) ABSTRACT

An ingestible material delivery device for sequentially delivering first and second ingestible materials to a user through a feeding tube provides a tube body having first and second chambers separated by a seal. A puncture tool is disposed in the second chamber extending toward the seal. The puncture tool engages and disrupts the seal when the second chamber is compressed. In some embodiments, the second chamber includes a plurality of interconnected bellows operable for axial compression of the second chamber. Another embodiment of a delivery device provides a tube body having first and second chambers with exit nozzles extending in opposite flow directions. A method of sequentially delivering first and second ingestible materials to a user through a feeding tube is also provided.

13 Claims, 6 Drawing Sheets

COMPRESSIBLE MULTI-CHAMBER FEEDING TUBE DELIVERY DEVICE AND METHODS

BACKGROUND

1. Technical Field

The present disclosure relates generally to devices and methods for delivering ingestible materials into a user's body and more particularly to mechanical devices and methods for delivering ingestible materials to a user's gastrointestinal tract through a feeding tube.

2. Background Art

In many applications, a patient may be unable to orally consume ingestible materials such as food products, nutritional supplements or medications and must be intubated with a feeding tube for delivery of such products. Intubation generally involves placing a feeding tube through the mouth or nose, beyond the esophagus, and extending to a position in the user's gastrointestinal tract, typically the stomach. Conventional feeding tubes typically include a tube inlet located outside the user's body and a tube outlet positioned inside the user's body. Ingestible materials injected into the feeding tube can be passed through the tube outlet directly to the stomach or other gastrointestinal location for consumption by the user.

In many applications, it is desirable to inject an ingestible material through a feeding tube into a user's body using a delivery device. One common application involves the use of a nasogastric feeding tube. A nasogastric feeding tube generally extends through the patient or user's nostril, nasopharynx, oropharynx, and esophagus into the user's stomach or intestine. Devices for delivering ingestible materials to a user through a nasogastric tube inlet using a plunger-driven delivery device, or syringe, are known in the art. However, such conventional plunger-driven feeding tube delivery devices include numerous moving parts that add complexity and cost to device manufacturing and packaging processes, as well as complicating use.

Another problem associated with conventional plunger-driven feeding tube delivery devices involves incomplete advancement of the ingestible material through the feeding tube. Generally, the feeding tube can have a length from about 10-100 cm, depending on the size of the patient and the particular application. When an ingestible material is injected into the feeding tube, the material must be pushed through the entire length of the feeding tube to the tube outlet inside the user's body. In some applications, a plunger-driven feeding tube delivery device is not capable of pushing the entire ingestible material volume completely through the entire length of the feeding tube using only one stroke of the plunger. Instead, using conventional devices and methods, some ingestible material may remain in the tube after the plunger has been fully depressed in a single stroke, thereby forming an occlusion in the tube and forcing the user to perform additional steps to completely evacuate the tube. Such additional steps add complexity to the process of administering ingestible material through the feeding tube. In many instances, users of conventional plunger-driven feeding tube delivery devices must disconnect the delivery device and attach a second device that includes a flushing liquid to push the remaining material through the feeding tube. Such disconnection and reconnection adds additional steps and requires that a sterile second flushing device be kept on hand at all times.

Another problem associated with conventional plunger-driven feeding tube delivery devices includes the growth and development of microorganisms in the feeding tube following delivery of the ingestible material through the tube. In some applications, the ingestible material includes chemical compounds that can promote the growth of bacteria in the interior of the tube. Conventional devices can leave ingestible material deposits on the interior wall of the tube following delivery, creating regions that support bacterial growth. Such bacterial growth can pose health risks to the user as subsequent injections into the tube will likely introduce the bacteria into the body. Additionally, in some applications, conventional syringe or plunger-driven devices do not fully evacuate the feeding tube following administration of the ingestible material, causing biofilm formation on the interior of the feeding tube. In many applications, a compressible multi-chamber delivery device for sequentially administering ingestible materials would be superior to existing conventional delivery devices with respect to the noted problems of conventional devices.

Thus, there is a continuing need in the art for improvements in feeding tube delivery devices and methods for introducing ingestible materials into a user's body through a feeding tube.

BRIEF SUMMARY

One aspect of the present disclosure provides an apparatus for sequentially delivering first and second ingestible materials to a user through a feeding tube. The device includes a first chamber defined in the delivery device and a second chamber co-axially aligned with the first chamber defined in the delivery device. A passage is defined between the first and second chambers, and a breakable seal is disposed across the passage. A puncture tool extends from the second chamber toward the seal. The first and second chambers are both compressible for manually forcing ingestible material from the delivery device into the feeding tube.

Yet another embodiment of the present disclosure provides an ingestible material delivery device for a feeding tube. The device includes a tube body and a first radially-compressible chamber defined in the tube body. A second radially-compressible chamber is also defined in the tube body. A first tube fitting is attached to the first chamber, and a second tube fitting is attached to the second chamber. The first tube fitting defines a first flow direction, and the second tube fitting defines a second flow direction. The first and second flow directions are substantially opposite in some embodiments.

A further embodiment of the present disclosure provides a method of sequentially administering first and second ingestible materials to a user through a feeding tube. The method includes the steps of: (a) providing an ingestible material delivery device including first and second chambers, each filled with an ingestible material, the delivery device including a seal between the first and second chambers and a puncture tool positioned in the second chamber extending toward the seal; (b) attaching a feeding tube to the first chamber; (c) compressing the first chamber; and (d) compressing the second chamber, causing the puncture tool to disrupt the seal.

Yet another embodiment of the present disclosure provides a method of manufacturing a dual-chamber delivery device for sequentially delivering first and second ingestible materials to a user through a feeding tube. The method includes the steps of: (a) blow molding a tube body having first and second axially consecutive chambers and a passage defined between the chambers; (b) filling the second chamber with a second ingestible material; (c) applying a breakable seal across the passage; and (d) filling the first chamber with a first ingestible material.

Numerous other objects, features and advantages of the present disclosure will be readily apparent to those skilled in the art upon a reading of the following description when taken in conjunction with the accompanying drawings.

DETAILED DESCRIPTION

Figure 1:
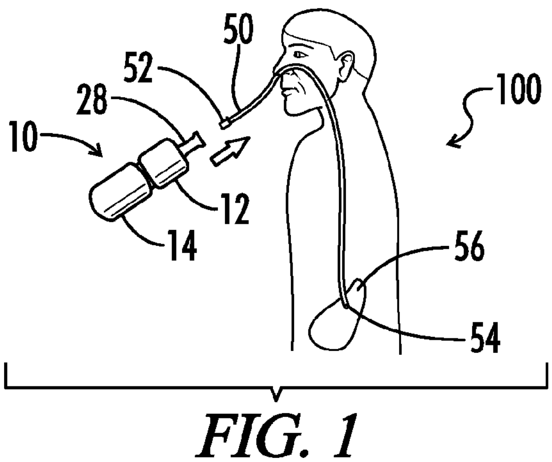
FIG. 1 illustrates partial cross-sectional view of an embodiment of a delivery device being connected to a feeding tube inserted in a user's body in accordance with the present disclosure.

Referring now to the drawings and particularly to FIG. 1, a view of an embodiment of a dual chamber ingestible material delivery device for a feeding tube is generally shown and is designated by the numeral 10. In the drawings, not all reference numbers are included in each drawing, for the sake of clarity. In addition, positional terms such as "upper," "lower," "side," "top," "bottom," "vertical," "horizontal," etc. refer to the delivery device when in the orientation shown in the drawing. The skilled artisan will recognize that delivery devices in accordance with the present disclosure can assume different orientations when in use, or during handling, shipping or storage.

As seen in FIG. 1, a feeding tube 50 is positioned in the body of a user 100. The feeding tube 50 can include an enteral or parenteral feeding tube having a tube inlet 52 and a tube outlet 54. The tube inlet 52 can include an inlet fitting such as a luer connector, a press-fit connector, a threaded connector, a barb connector or any other suitable tube connector known in the art. Feeding tube 50 in some embodiments, as seen in FIG. 1, includes a nasogastric tube inserted into a nostril of user 100 and extending through the user's gastrointestinal tract to the user's stomach 56. Typically, the tube outlet 54 is positioned in or near the user's stomach 56 and the tube inlet 52 is positioned outside the user's body. Also seen in FIG. 1, in some embodiments, a dual-chamber ingestible material delivery device 10 can be mechanically connected to the tube inlet 52 via a connection fitting 28 disposed on or attached to the delivery device 10. The delivery device 10 can be manually actuated by user 100, or by another individual such as a medical professional, a nurse, a caretaker, etc. to deliver ingestible material to the user 100 through the feeding tube 50. In some embodiments, user 100 may be unconscious or unable to consume food orally, thus requiring the use of feeding tube 50 for delivery of food products, nutritional supplements, and/or medications.

Figure 2A:
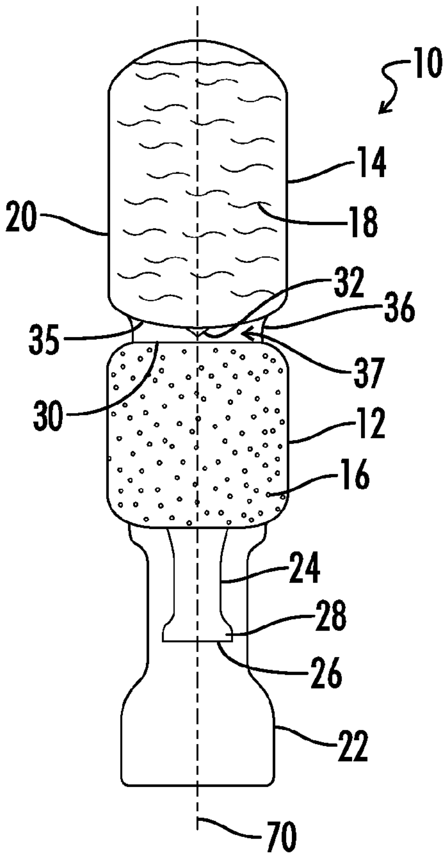
FIG. 2A illustrates an elevation view of an embodiment of delivery device filled with first and second ingestible materials in accordance with the present disclosure.

As seen in FIG. 2A, delivery device 10 includes a first chamber 12 and second chamber 14. First and second chambers 12, 14 are axially aligned along chamber axis 70. First and second chambers 12, 14 form a tube body 20 operative for storing one or more ingestible materials. Tube body 20 can include a material such as a plastic or polymer that can be compressed or deformed such that first and second chambers can be manually squeezed by a user in a radial direction generally toward chamber axis 70 by a user. Tube body 20 can be formed by blow molding processes including but not limited to extrusion blow molding, injection blow molding and stretch blow molding. Tube body 20 can also be formed using other suitable manufacturing processes known in the art or hereinafter developed.

First and second chambers 12, 14 are interconnected by a bridge member 36. In some embodiments, a passage 37 is defined between first and second chambers 12, 14 such that material can flow from second chamber 14 into first chamber 12.

A seal 30 is disposed between first and second chambers 12, 14 across passage 37. Seal 30 can include an integral portion of a longitudinal end wall of first chamber 12 in some embodiments. In other embodiments, seal 30 can include a dissimilar material spanning a hole defined in a longitudinal end wall of first chamber 12 adjacent bridge member 36. Seal 30 functions to prevent material stored in first chamber 12 from mixing with material stored in second chamber 14 prior to breakage of the seal 30. Seal 30 can be referred to as a friable seal 30 in some applications because seal 30 can be broken by the application of force.

A first ingestible material 16 can be disposed in first chamber 12, and a second ingestible material 18 is disposed in second chamber 14. In some embodiments, one or both ingestible materials 16, 18 include a food product, a nutritional formula, a nutritional supplement and/or a pharmaceutical compound. In other embodiments, one or both ingestible materials 16, 18 form a solid. In other embodiments, ingestible materials 16, 18 can include a powder or particulate material that is intended to be mixed with the material stored in the other chamber. Ingestible materials 16, 18 can include an amorphous solid such as a gel or a paste. One or more prebiotic materials that promote the growth and development of bacteria in the digestive tract, such as but not limited to a galactooligosaccharide (GOS) or a fructooligosaccharide (FOS), can be included in first or second ingestible materials 16, 18. Other suitable prebiotic or probiotic materials and mixtures known in the art or hereinafter developed can be included in ingestible materials 16, 18 in some embodiments.

In a preferred embodiment, first ingestible material 16 stored in first chamber 12 includes a food product, a nutritional supplement and/or a pharmaceutical compound, and second ingestible material 18 stored in second chamber 14 includes a flushing liquid for advancing first ingestible material 16 through a feeding tube. First ingestible material 16 can include an active product, and second ingestible material 18 can include a sterile, non-active flush.

The presence of first ingestible material 16 in a feeding tube 50 can contribute to the growth and development of bacteria on the inner wall of the feeding tube. Such bacterial growth and development presents a threat of contamination to the user and is generally undesirable. Additionally, after one or more uses, feeding tube 50 may develop a biofilm on the interior tube wall. Such a biofilm may include one or more types of bacteria and can pose a health hazard to the user. Bacteria and biofilm growth and development can be prevented by sequentially forcing a second ingestible material 18 including a flushing liquid through feeding tube 50 after passage of first ingestible material 16 through feeding tube 50. Second ingestible material 18 including a flushing liquid contained in second chamber 14 can perform one or more functions when injected into the feeding tube 50. First, the flushing liquid can push first ingestible material 16 through feeding tube 50 into the user's stomach 56. Second, the flushing liquid can disinfect the interior feeding tube wall to inhibit bacterial growth and development. Third, the flushing liquid can prevent biofilm growth and development on the interior feeding tube wall. It is understood that the flushing liquid can perform as few as one or as many as all of these functions in various embodiments.

In some embodiments, the flushing liquid included in second ingestible material 18 comprises water. In further embodiments, the flushing liquid includes a disinfectant material or an antimicrobial agent for killing and/or preventing the growth of microorganisms such as bacteria in feeding tube 50.

Figure 3A:
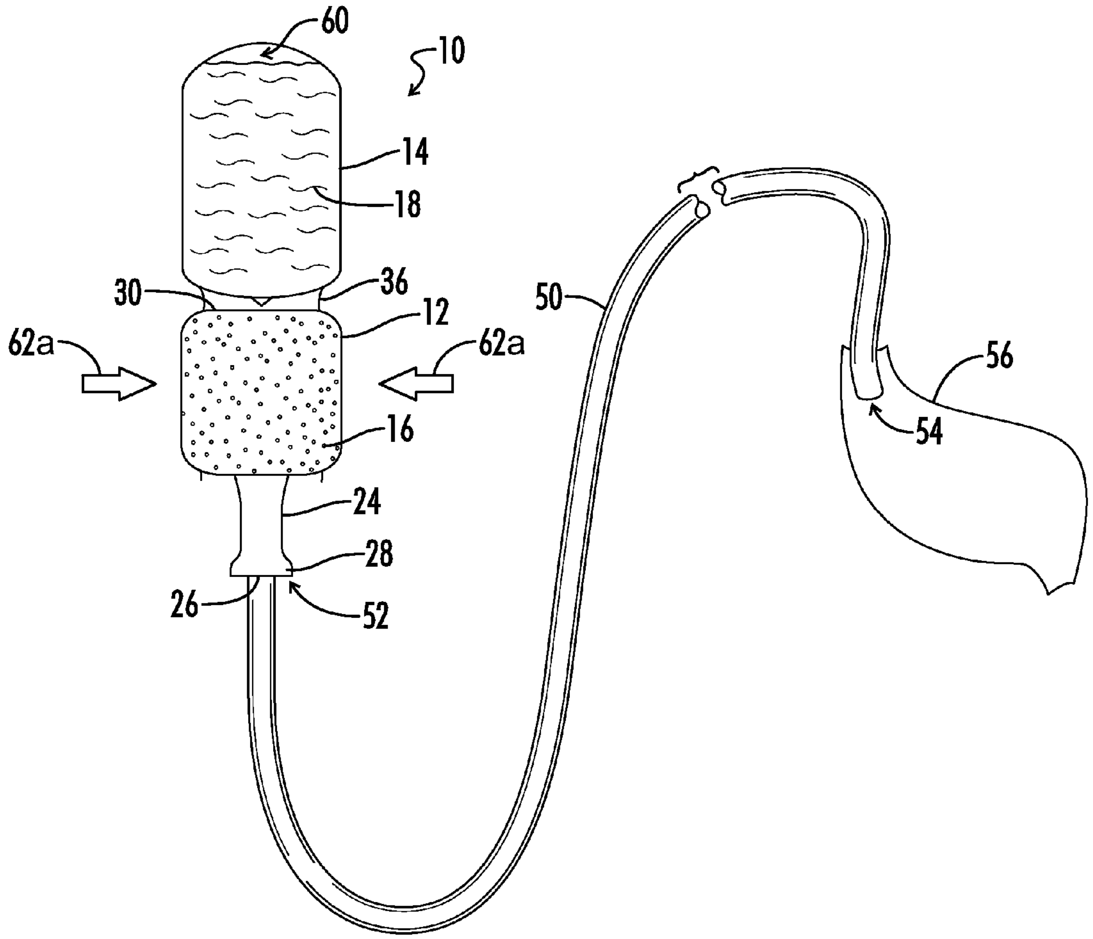
FIG. 3A illustrates a partially broken-away view of the embodiment of a delivery device of FIG. 3A connected to a feeding tube in accordance with the present disclosure.

As seen in FIG. 3A, in some embodiments a second chamber gas pocket 60 can be included in second chamber 14. Second chamber gas pocket 60 provides a gas volume that can push the flushing liquid and the first ingestible material further along feeding tube 50 toward stomach 56. In some applications, a first chamber gas pocket 58 can be included in first chamber 12.

Also seen in FIG. 2A, delivery device 10 includes an exit nozzle 24 including a tube fitting 28. Exit nozzle 24 forms a channel for passage of first and second ingestible materials 16, 18 from delivery device 10 in some embodiments. Tube fitting 28 is generally formed on the distal end of exit nozzle 24 and can include a mechanical attachment structure for connecting delivery device 10 to a feeding tube inlet 52. In some embodiments, tube fitting 28 can include a male or female luer connector, a threaded connector, a press-fit connector or any other suitable type of hose connector or fitting known in the art. Exit nozzle 24 generally defines an exit orifice 26 positioned for ejecting first and/or second ingestible materials 16, 18.

Figure 4A:
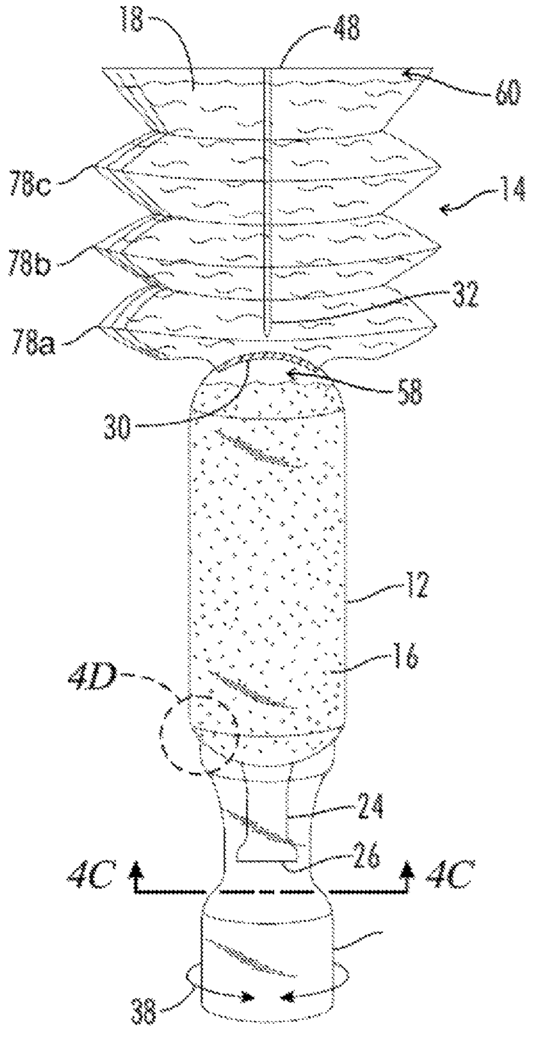
FIG. 4A illustrates perspective view of an embodiment of a delivery device with an axially compressible second chamber in accordance with the present disclosure.
Figure 4B:
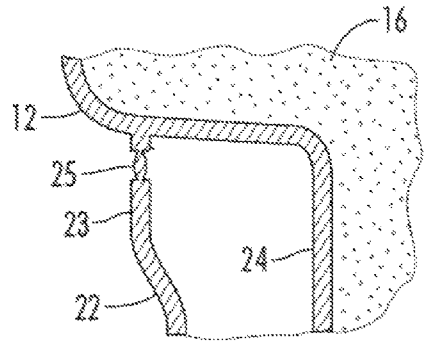
FIG. 4B illustrates a partial cross-sectional view of an embodiment of a frangible bridge in accordance with the present disclosure.
Figure 4C:
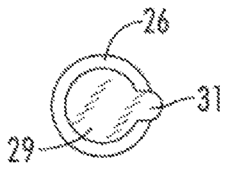
FIG. 4C illustrates an end view of Section 4C-4C from FIG. 4A.

As seen in FIG. 4C, in some embodiments, an orifice seal 29 can be positioned on exit orifice 26 covering the opening. Orifice seal 29 can include a peel tab 31 for manually removing orifice seal 29 in some embodiments. Orifice seal 29 can include a metal foil, a polymer, a plastic or any other suitable material for sealing exit orifice 26 for preventing leakage or contamination of the stored product.

Figure 2B:
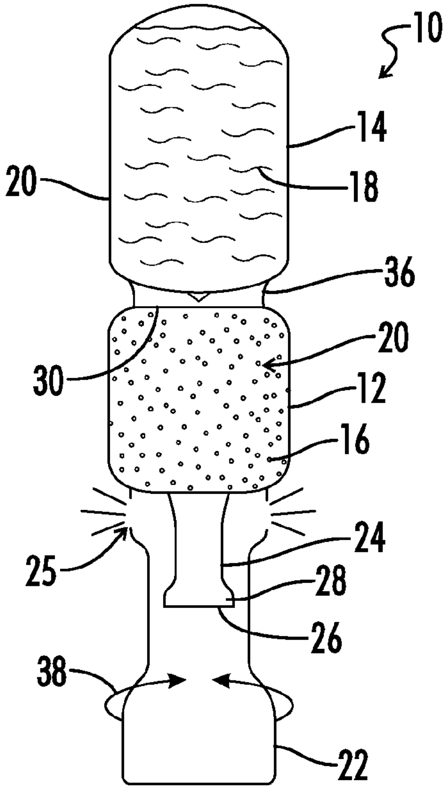
FIG. 2B illustrates an elevation view of the embodiment of a delivery device of FIG. 2A with a removable cap being removed.

Referring further to FIG. 2A and FIG. 2B, delivery device 10 includes a removable cap 22. Removable cap 22 generally houses and protects exit nozzle 24, tube fitting 28 and exit orifice 26 from contamination and/or damage. Removable cap 22 can include a plastic or polymer and can be disposable or reusable. Removable cap 22 can include a hollow cap structure defining an interior cap void attached to first chamber 12, wherein interior cap void houses exit nozzle 24 when cap 22 is attached to first chamber 12. Removable cap 22 in some embodiments can be removed from delivery device 10 by twisting or rotating cap 22 about chamber axis 70. In some embodiments, removable cap 22 includes internal cap threads, and first chamber 12 includes corresponding chamber threads such that cap threads engage chamber threads. As such, cap 22 can be threadedly removed from and installed on device 10 in some embodiments.

Figure 4D:
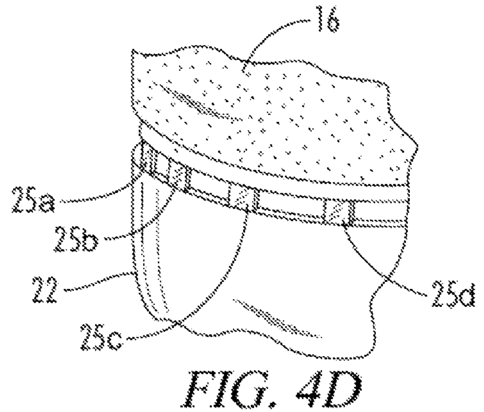
FIG. 4D illustrates a partial perspective view of Section 4D from FIG. 4A.

In further embodiments, cap 22 is attached to first chamber 12 using one or more frangible bridges 25, illustrated in FIG. 2B and FIG. 4D. Each frangible bridge 25*a*, 25*b*, 25*c*, 25*d*, etc. extends between a cap rim 23 defined on the edge of cap 22 and a chamber rim defined on first chamber 12, seen in an embodiment in FIG. 4B. Each frangible bridge 25*a*, 25*b*, etc. is dimensioned such that one or more bridges can be broken when cap 22 is rotated relative to first chamber 12 in a rotation direction 38, seen for example in FIG. 2B.

In additional embodiments, an annular tamper-evident ring or band can be disposed between cap 22 and first chamber 12 to visually indicate to a user whether cap 22 has previously been removed. Each frangible bridge 25*a*, 25*b*, etc. can extend from the tamper-evident ring to the cap 22 in some embodiments. A retaining structure can be positioned on the first chamber 12 to retain the tamper-evident ring on the first chamber 12 when the cap 22 is rotated relative to the first chamber 12.

Figure 3B:
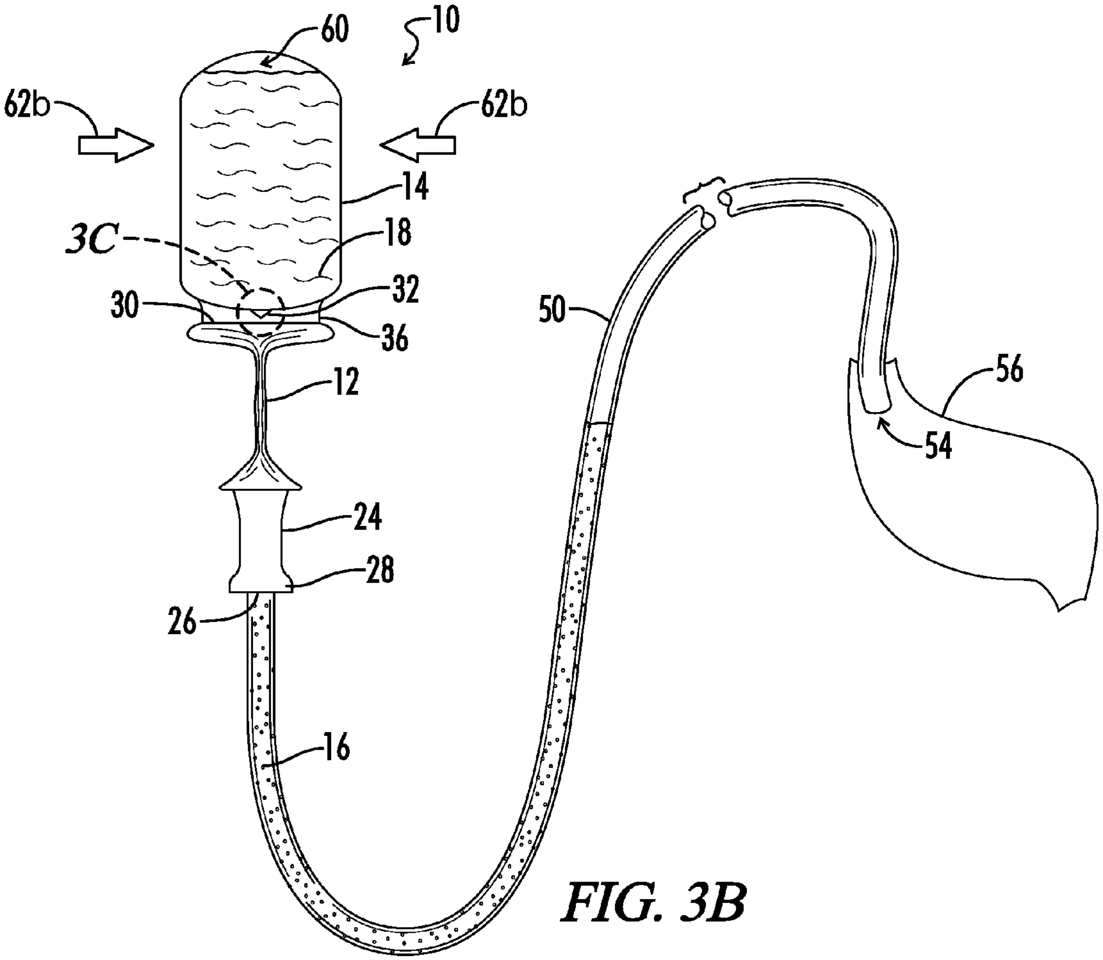
FIG. 3B illustrates a partially broken-away view of the embodiment of a delivery device of FIG. 3A having a compressed first chamber.

Referring now to FIG. 3A, in some embodiments, feeding tube 50 can be mechanically attached to exit nozzle 24 after the cap has been removed. Tube inlet 52 generally engages tube fitting 28 such that ingestible material can pass from first chamber 12 to feeding tube 50. As seen in FIG. 3A, in one mode of operation, a user can apply a radial force 62*a* against first chamber 12, thereby forcing first ingestible material 16 through exit nozzle 24, out exit orifice 26 and into feeding tube 50, as seen in FIG. 3B. Radial compression of first chamber 12 can be achieved by manually squeezing first chamber 12 with a user's hand. In other embodiments, first chamber 12 can be radially compressed using a machine or other structure.

In some embodiments, after first chamber 12 has been radially compressed, a volume of first ingestible material 16 may remain in feeding tube 16, forming an occlusion in the tube. Thus, second ingestible material 18 must be forced into the feeding tube 50 to push the occlusion of first ingestible material 16 into the user's stomach 56.

Figure 3C:
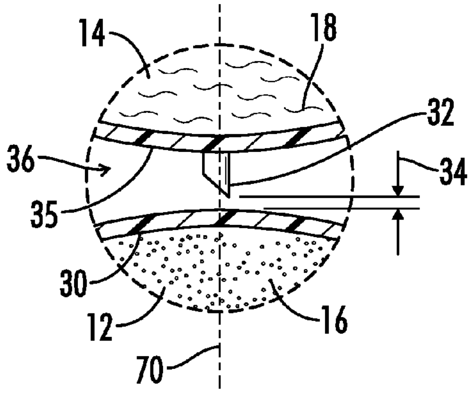
FIG. 3C illustrates a partial cross-sectional view of Section 3C-3C of FIG. 3B showing an embodiment of a puncture tool

Second ingestible material 18 is generally prevented from entering first chamber 12 and feeding tube 50 by seal 30. In some embodiments, such as those illustrated in FIGS. 1-5, seal 30 must be disrupted for second ingestible material 18 to enter feeding tube 50, A puncture tool 32 is disposed between first and second chambers 12, 14. Puncture tool 32 in some embodiments is positioned on a tool wall 35. Tool wall 35 can span second chamber 14 substantially transverse to chamber axis 70. Puncture tool 32 includes a sharpened point axially projecting toward seal 30. A gap 34 is defined between puncture tool 32 and seal 30, as seen in FIG. 3C. Gap 34 can range from a few microns to several millimeters in some embodiments. Puncture tool 32 in some embodiments can be integrally formed in second chamber 14 and can include a rigid material projecting toward first chamber 12. In other embodiments, puncture tool 32 can include a metal or other suitable rigid material attached to second chamber 14 or to tool wall 35.

A second radial force 62*b* can be applied to second chamber 14. When second radial force 62*b* is applied to second chamber 14, puncture tool 32 advances axially toward seal 30. When a sufficient level of second radial force 62*b* is applied to second chamber 14, puncture tool 32 advances fully across gap 34 and punctures seal 30. Once seal 30 is punctures, second ingestible material 18 passes through first chamber 12, through exit nozzle 24 and into feeding tube 50. Once in feeding tube 50, second ingestible material 18 can interact or mix with first ingestible material in some embodiments. Additionally, second ingestible material 18 in some embodiments can mechanically push, or flush, first ingestible material through feeding tube 50 into the user's stomach. In some embodiments, an increased internal chamber pressure is developed in second chamber 14 due to the application of radial force 62 up until the moment when the seal 30 is disrupted. When the seal is disrupted, the increased internal chamber pressure is released through the first chamber, and the sudden release of the internal chamber pressure due to the seal breakage can cause second ingestible material 18 to be forcefully ejected from exit orifice 26 into feeding tube 50. Such forceful ejection due to the sudden disruption of seal 30 can further enhance the flushing function of second ingestible material 18 to push first ingestible material 16 through the feeding tube 50.

Referring now to FIG. 4A, a second embodiment of a delivery device 10 in accordance with the present disclosure provides an axially compressible second chamber 14. In this alternative embodiment, delivery device 10 includes a first chamber 12 as described above. A seal 30 spans a longitudinal end wall of first chamber 12 adjacent second chamber 14. Seal 30 prevents first ingestible material 16 from mixing with second ingestible material 18 until seal 30 is broken. Additionally, a cap 22 can be disposed on first chamber 12 as described above.

As seen in FIG. 4A, second chamber 14 includes an axially compressible chamber including a plurality of interconnected bellows 78*a*, 78*b*, 78*c*, etc. A base 48 provides a surface against which a user can apply an axial force to compress the plurality of interconnected bellows 78*a*, 78*b*, 78*c*, etc. toward the first chamber 12. A puncture tool 32 is disposed in second chamber 14 protruding from base 48 toward seal 30 in some embodiments.

Figure 5A:
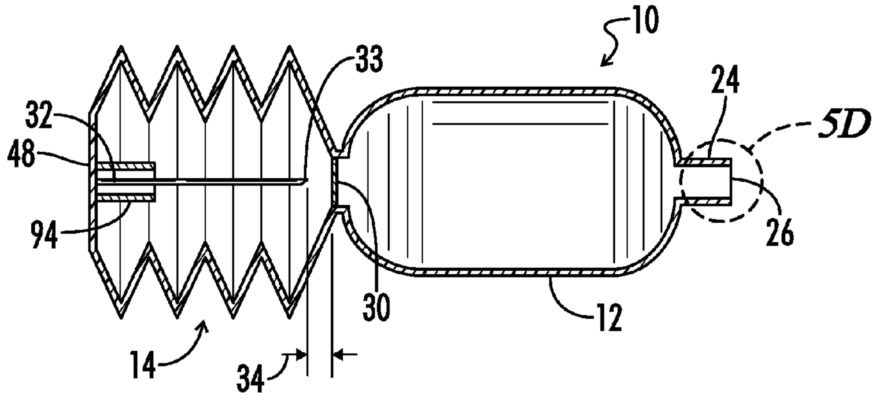
FIG. 5A illustrates a partial cross-sectional view of an embodiment of a delivery device including a bellows-type second chamber.
Figure 5B:
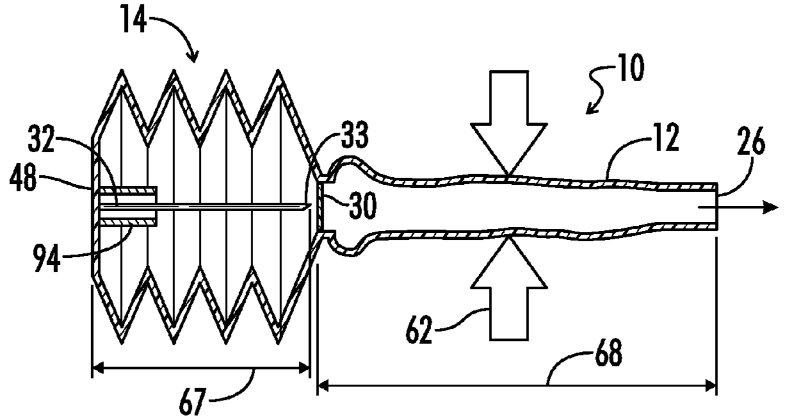
FIG. 5B illustrates a cross-sectional view of the embodiment of a delivery device including a bellows-type second chamber of FIG. 5A.
Figure 5D:
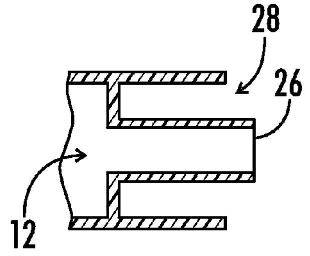
FIG. 5D illustrates a detail cross sectional view of an embodiment of an outlet fitting.

A cross-sectional view of this embodiment of a delivery device 10 is illustrated generally in FIG. 5A. A gap 34 can be disposed between the distal tip 33 of puncture tool 32 and seal 30. During use, exit nozzle 24 can be connected to a feeding tube. In some embodiments, as seen in FIG. 5D, a luer connector is formed on tube fitting 28 for attachment to a feeding tube. After connection to a feeding tube, a radial force 62 is applied to first chamber 12, as seen in FIG. 5B. The radial force 62 forces first ingestible material 16 through exit orifice 26 into the feeding tube.

Next, an axial force 64 is applied to base 48 of second chamber 14. Axial force 64 applied to second chamber 14 causes the bellows 78*a*, 78*b*, etc. to compress toward first chamber and simultaneously causes puncture tool 32 to advance toward seal 30. Puncture tool 32 engages seal 30, creating an opening through which second ingestible material 18 can advance into first chamber 12 and on into the feeding tube.

In some embodiments, as puncture tool 32 travels axially across gap 34, an increasing internal chamber pressure is developed in second chamber 14 resulting from a decrease in the volume of second chamber 14 due to the application of axial force 64. The increasing internal chamber pressure is suddenly released seal 30 is disrupted. Such sudden release of the internal chamber pressure in second chamber 14 can cause second ingestible material 18 to be forcefully ejected from second chamber 14, through first chamber 12, out exit orifice 26 and through feeding tube 50, thereby driving first ingestible material 16 into the user's stomach. In other embodiments, the sudden release of internal chamber pressure is negligible, and the driving force associated with advancing second ingestible material is due solely to the controlled deformation of second chamber 14. The gap 34 distance is a control parameter that can be used to determine whether a second chamber pressure is developed prior to seal breakage.

In some embodiments, puncture tool 32 defines an axial tool length 67. First chamber generally defines a first chamber axial length 68 between seal 30 and exit orifice 26. In some embodiments, first chamber axial length 68 is greater than axial tool length 67 such that puncture tool 32 does not protrude beyond exit orifice 26 when second chamber 14 is in the fully compressed position. This dimensional relationship between axial tool length 67 and first chamber axial length 68 in some embodiments prevents possible user injury that could be caused by a sharp point protruding from exit orifice 26. Similarly, in some embodiments, delivery device 10 includes a total compressed length 66 defined after both first and second chambers 12, 14 have been compressed in their respective compression directions. In some embodiments, total compressed length 66 is greater than axial tool length 67.

Figure 5C:
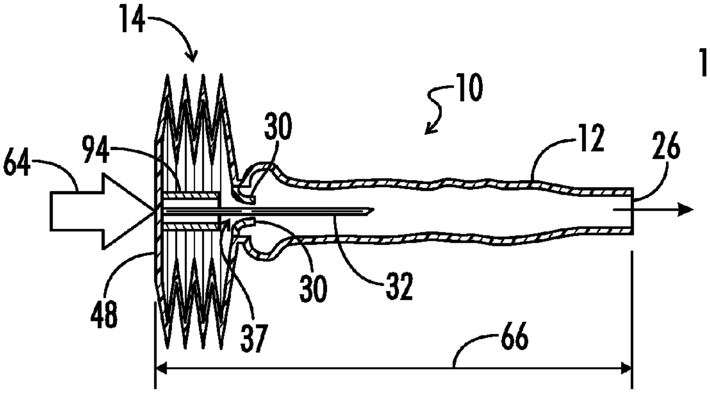
FIG. 5C illustrates a cross-sectional view of the embodiment of a delivery device of FIG. 5A with an axially-compressed second chamber.

As seen in FIGS. 5A-5C, in some embodiments, a puncture tool support 94 can extend from base 48 partially surrounding puncture tool 32. Puncture tool support 94 can be integrally formed on base 48 or can be a separate piece attached to base 48. Puncture tool support defines an inner diameter greater than the outer diameter of puncture tool 32. Puncture tool support 94 prevents puncture tool 32 from becoming angularly misaligned inside second chamber 14. Thus, puncture tool support 94 prevents puncture tool 32 from moving and prevents puncture tool 32 from becoming misaligned with seal 30. Puncture tool support 94 can include an axial length no greater than the compressed length of second chamber 14, as seen in FIG. 5C.

Figure 6:
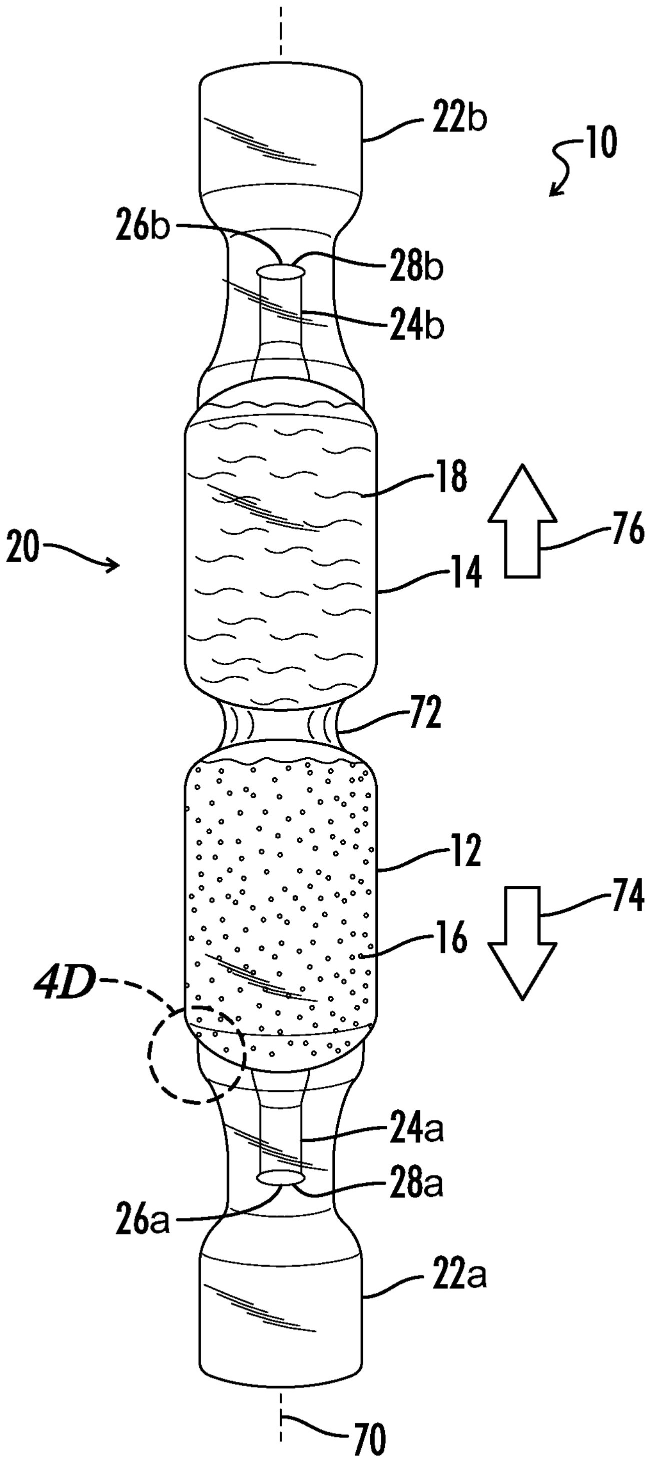
FIG. 6 illustrates an elevation view of an embodiment of a delivery device with multiple exit openings.

Referring now to FIG. 6, a third embodiment of the present disclosure provides a dual-chamber feeding tube delivery device 10 adapted to selectively eject first and second ingestible materials sequentially in opposite axial directions. This embodiment includes a first chamber 12 and a second chamber 14. First and second chambers 12, 14 in some embodiments extend coaxially along chamber axis 70. First and second chambers 12, 14, can include different axial chamber lengths, different chamber diameters and/or different chamber volumes in some embodiments. First chamber 12 generally contains a first ingestible material 16, and second chamber 14 contains a second ingestible material 18.

First and second chambers 12, 14 are connected by a rigid linkage 72. Rigid linkage 72 does not include any internal passage for material to pass between first and second chambers 12, 14. In some embodiments, rigid linkage 72 is a separate member that is attached to both first and second chambers 12, 14 on opposite sides. In other embodiments, rigid linkage 72 is integrally formed, or integrally molded, in tube body 20 between first and second chambers 12, 14.

In this embodiment, a first exit nozzle 24*a* extends axially from the first chamber 12, and a second exit nozzle 24*b* extends axially from second chamber 14 opposite first exit nozzle 24*a*. First exit nozzle 24*a* includes a first tube fitting 28*a* and a first exit orifice 26*a*. Second exit nozzle 24*b* includes a second tube fitting 28*b* and a second exit orifice 26*b*. A first removable cap 22*a* is attached to first chamber 12, and a second removable cap 22*b* is attached to second chamber 14.

During use, first removable cap 22*a* is removed from delivery device 10, and first exit nozzle 24*a* is mechanically attached to a feeding tube via first tube fitting 28*a*. A radial force is then applied against first chamber 12, and first ingestible product 16 is ejected from first chamber 12 into the feeding tube. Subsequently, first tube fitting 28*a* is disengaged from the feeding tube. The second cap 22*b* can be removed from the second chamber 14 before or after the first ingestible material 16 is evacuated into the feeding tube. The user can manually flip the delivery device 10 one-hundred-eighty degrees such that second exit nozzle 24*b* is oriented toward the feeding tube. Second exit nozzle 24*b* can be mechanically attached to the feeding tube via second tube fitting 28*b* after the first exit nozzle 24*a* has been disconnected. Next, a second radial force can be applied against second chamber 14, causing second ingestible material 18 to be ejected from second chamber 14, through second exit nozzle 24*b* and into the feeding tube.

Dual-chamber delivery device 10 illustrated in FIG. 6 is characterized in that first chamber 12 defines a first flow direction 74, and second chamber 14 defines a second flow direction 76. In some embodiments, the first and second flow directions 74, 76 are directly opposite each other. In additional embodiments, the first and second flow directions 74, 76 are angularly offset.

In many applications, a delivery device in accordance with the various embodiments disclosed herein can be provided being pre-filled with metered doses of first and second ingestible materials contained in first and second chambers.

It will be readily understood by those of skill in the art that the principles of the present disclosure can be applied to delivery devices in embodiments having more than two chambers.

The present disclosure further provides methods of sequentially delivering ingestible materials to a user through a feeding tube. One embodiment of a method of sequentially administering first and second ingestible materials to a user through a feeding tube includes the steps of: (a) providing an ingestible material delivery device including first and second chambers, each filled with an ingestible material, the delivery device including a seal between the first and second chambers and a puncture tool positioned in the second chamber extending toward the seal; (b) attaching a feeding tube to the first chamber; (c) compressing the first chamber; and (d) compressing the second chamber, causing the puncture tool to disrupt the seal. In some embodiments, step (c) further comprises radially compressing the first chamber. In additional embodiments, step (d) further comprises axially compressing the second chamber.

A further embodiment of the present disclosure provides a method of manufacturing a dual-chamber delivery device for sequentially delivering first and second ingestible materials to a user through a feeding tube. The method includes the steps of: (a) blow molding a tube body having first and second axially consecutive chambers and a passage defined between the chambers; (b) filling the second chamber with a second ingestible material; (c) applying a breakable seal across the passage; and (d) filling the first chamber with a first ingestible material. In some embodiments, the method of manufacturing a dual-chamber delivery device further comprises the step of (e) positioning a puncture tool in the second chamber projecting toward the first chamber, the puncture tool defining a gap between the puncture tool and the seal.

Thus, although there have been described particular embodiments of the present disclosure of a new and useful Compressible Multi-Chamber Feeding Tube Delivery Device and Methods, it is not intended that such references be construed as limitations upon the scope of the disclosure except as set forth in the following claims.

What is claimed is:

1. An apparatus for sequentially delivering first and second ingestible materials to a user through a feeding tube, comprising:
- a delivery device;
- a first chamber defined in the delivery device;
- a second chamber co-axially aligned with the first chamber defined in the delivery device;
- a passage defined between the first and second chambers;
- a breakable seal disposed across the passage; and
- a puncture tool extending from the second chamber toward the seal, wherein the puncture tool disrupts the seal when the second chamber is radially compressed.

2. The apparatus of claim 1, further comprising:
- an exit nozzle extending axially from the first chamber opposite the second chamber, the exit nozzle defining an exit orifice; and
- a tube fitting disposed on the exit nozzle, the tube fitting shaped to mechanically engage the feeding tube.

3. The apparatus of claim 2, further comprising:
- a removable cap disposed on the first chamber, surrounding the exit nozzle.

4. The apparatus of claim 3, further comprising:
- a plurality of frangible bridges disposed between the removable cap and the first chamber.

5. The apparatus of claim 1, further comprising:
- a first ingestible material disposed in the first chamber; and
- a second ingestible material disposed in the second chamber.

6. The apparatus of claim 5, wherein the first ingestible material comprises a nutritional formula.

7. The apparatus of claim 5, wherein the first ingestible material comprises a food product.

8. The apparatus of claim 5, wherein the first ingestible material comprises a pharmaceutical compound.

9. The apparatus of claim 5, wherein:
- the second ingestible material comprises a flushing liquid.

10. The apparatus of claim 9, wherein the second ingestible material comprises an antimicrobial agent.

11. The apparatus of claim 10, wherein:
- the first ingestible material comprises a first pharmaceutical compound; and
- the second ingestible material comprises a second pharmaceutical compound.

12. A method of sequentially administering first and second ingestible materials to a user through a feeding tube, comprising:
- (a) providing an ingestible material delivery device including first and second chambers, the second chamber being co-axially aligned with the first chamber, each filled with an ingestible material, the delivery device including a passage defined between the first and second chambers, a seal between the first and second chambers the seal being disposed across the passage, and a puncture tool positioned in the second chamber extending toward the seal;
- (b) attaching a feeding tube to the first chamber;
- (c) compressing the first chamber; and
- (d) radially compressing the second chamber, causing the puncture tool to disrupt the seal.

13. The method of claim 12, wherein step (c) further comprises radially compressing the first chamber.

* * * * *